United States Patent [19]

Nagaoka et al.

[11] Patent Number: 5,604,210
[45] Date of Patent: Feb. 18, 1997

[54] INHIBITOR OF VASCULAR PERMEABILITY ENHANCER

[75] Inventors: Akinobu Nagaoka, Kawanishi; Tetsuji Imamoto, Kitakatsuragi-gun; Tsuneo Asano, Kawanishi; Yoshihiro Sugiura, Tsurumai-nishimachi; Giichi Goto, Osaka, all of Japan

[73] Assignee: Takeda Chemical Industries, Ltd., Osaka, Japan

[21] Appl. No.: 456,723

[22] Filed: Jun. 1, 1995

[30] Foreign Application Priority Data

Jun. 2, 1994 [JP] Japan .................... 6-120947

[51] Int. Cl.⁶ .................................................. A61K 31/70
[52] U.S. Cl. ............................................................. 514/46
[58] Field of Search ........................................... 514/46

[56] References Cited

U.S. PATENT DOCUMENTS

| | | | |
|---|---|---|---|
| 3,819,613 | 6/1974 | Marumoto et al. | 260/211.5 |
| 4,225,591 | 9/1980 | Marumoto et al. | 424/180 |
| 4,255,565 | 3/1981 | Marumoto et al. | 536/24 |
| 4,341,769 | 7/1982 | Marumoto et al. | 424/180 |

FOREIGN PATENT DOCUMENTS 58-83698 5/1983 Japan .

*Primary Examiner*—Raymond Henley, III
*Attorney, Agent, or Firm*—Fitzpatrick, Cella, Harper & Scinto

[57] ABSTRACT

The present invention relates to prevention or treatment a brain edema, an intracranial hemorrhage and a cerebral infarction by administering a pharmaceutically effective amount of a compound or a pharmaceutically acceptable salt thereof, for inhibiting a vascular permeability enhancer, which the compound is of the formula:

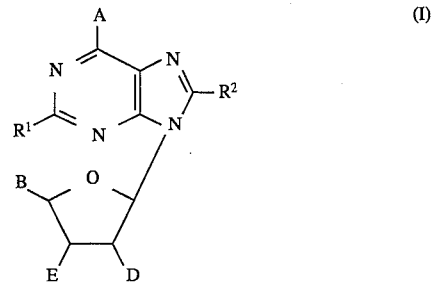

wherein
A is halogen, —X—$R^3$ in which X is O, S, NH or NHNH, and $R^3$ is H, acyl, a hydrocarbon group or an aromatic heterocyclic group, or —Y=$R^4$ in which Y is N or NHN, and $R^4$ is a divalent hydrocarbon group, and $R^1$ is H, halogen, a hydrocarbon group, a heterocyclic group or —Z—$R^5$ in which Z is O, S or NH, and $R^5$ is H, a hydrocarbon group or an aromatic heterocyclic group;

$R^2$ is H, halogen, a hydrocarbon group or a heterocyclic group;

B is —W—$R^6$ in which W is $CH_2$, CO or CS, and $R^6$ is OH, alkoxy, acyloxy, alkylsulfinyl, alkylsulfonyl, phosphoric acid or amino, or B together with E form a cyclic phosphoric ester; and D and E are H, amino, azido, halogen or OH.

28 Claims, No Drawings

INHIBITOR OF VASCULAR PERMEABILITY ENHANCER

BACKGROUND OF THE INVENTION

1. Field of the Invention

The present invention relates to a method for preventing or treating a brain edema, an intracranial hemorrhage (especially a recurrence of an intracranial hemorrhage and so on) and a cerebral infarction, which comprises administering a pharmaceutically effective amount of a compound which excellently inhibits a vascular permeability enhancer.

2. Description of the Prior Art

Stroke is a condition of a disease caused by a cerebrovascular disease, which includes a brain edema, an intracranial hemorrhage, a cerebral infarction, a transient ischemic attack, a subarachnoid hemorrhage, etc., each causing many kinds of diseases.

A brain edema occuring in an acute phase of a cerebrovascular disease, including that caused by a head injury, is a phenomenon wherein a blood brain barrier is damaged disorder by cerebral ischemia and the volume of the brain increases by an increase of a body fluid component in cerebral tissues, to which drug treatment such as an administration of a high dose of steroid in a short period and an intravenous injection of a hypertonic solution such as mannitol and glycerol have been generally applied.

A cerebral infarction is that necrosis of brain tissues is caused by a cerebrovascular blood flow disease, which is often caused by a cerebral thrombosis and a cerebral embolism.

On the other hand, a large number of nucleic acid derivatives have been synthesized so far and their pharmacological activities have been examined. And it has been reported that adenosine derivatives of some kind have a coronary vasodilation action and are useful as a medicament for treating an ischemic heart disease such as a coronary insufficiency, an angina pectoris and myocardial infarction, and a hyperpiesia (U.S. Pat. No. 3,819,613, U.S. Pat. No. 4,255,565, U.S. Pat. No. 4,225,591, U.S. Pat. No. 4,341,769 and JP-A-58 83698, etc.).

Furthermore, EP-0526866-A11 (disclosed in Feb. 10, 1993) describes that 5'-deoxy-5'-alkylthioadenosine such as 5'-deoxy-5'-methylthioadenosine (MTA) can be used for treating an ischemia with the results of the experiments using a heart ischemia model of rabbit.

Nowadays, steroids used for treating a brain edema have adverse effects such as bleeding of a digestive tract, abnormality of electrolyte metabolism, abnormality of sugar metabolism and complication of infections, while in an administration of the hypertonic solutions, stop of the administration causes phenomena such as another rise in cerebrospinal pressure, so that recently, they have not been used so often. Besides, a medicinal therapy of a cerebral hemorrhage is just a symptomatic treatment and there is no effective medicament to prevent a relapse of an intracranial hemorrhage. The same is true of a cerebral infarction. Under these circumstances, there is no medicament which is desirable from the viewpoint of effects or adverse effects in preventing or treating a brain edema, an intracranial hemorrhage and a cerebral infarction.

Therefore, development of medicaments which can prevent or treat a brain edema, an intracranial hemorrhage and a cerebral infarction, especially a relapse of them, has been desired.

SUMMARY OF THE INVENTION

The present inventors had earnestly studied and found that 5'-deoxy-5'-methylthioadenosine (MTA) extracted from a spontaneous cerebral apoplexy rat (SHRSP) strongly enhances a vascular permeability and that a compound having a chemical structure similar to the MTA represented by the formula:

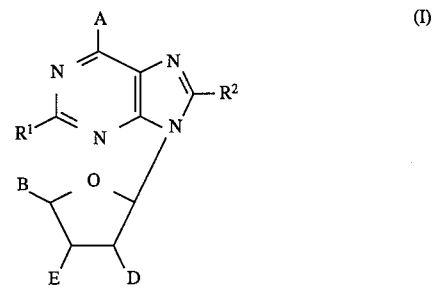

(I)

wherein

A is (i) a halogen atom, (ii) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group or (iii) —Y=$R^4$ in which —Y= is —N= or —NHN= and $R^4$ is an optionally substituted divalent hydrocarbon group;

$R^1$ is (i) a hydrogen atom, (ii) a halogen atom, (iii) an optionally substituted hydrocarbon group, (iv) an optionally substituted heterocyclic group or (v) —Z—$R^5$ in which —Z— is —O—, —S— or —NH— and $R^5$ is a hydrogen atom, an optionally substituted hydrocarbon group or an optionally subsituted aromatic heterocyclic group;

$R^2$ is a hydrogen atom, a halogen atom, an optionally substituted hydrocarbon group or an optionally substituted heterocyclic group;

B is —W—$R^6$ in which —W— is —$CH_2$—, >C=O or >C=S and $R^6$ is hydroxyl, or an optionally substituted alkoxy, acyloxy, alkylsulfinyl, alkylsulfonyl, O-phosphono or amino group, or B together with E may optionally form a cyclic phosphoric ester; and D and E are independently a hydrogen atom, an optionally substituted amino group, an azido group, a halogen atom or an optionally protected hydroxyl group, or a pharmaceutically acceptable salt thereof, selectively and strongly inhibits a vascular permeability enhancer in contrast with MTA contrary to expectation, so that it can be safely used for preventing or treating a brain edema and an intracranial hemorrhage, completing the present invention based on these.

The present invention relates to:

(1) a method for inhibiting a vascular permeability enhancer, which comprises administering a pharmaceutically effective amount of the compound (I) or a pharmaceutically acceptable salt thereof;

(2) a method of (1), which is for preventing or treating a cerebrovascular disease;

(3) a method of (2), wherein the disease is a brain edema, an intracranial hemorrhage or a cerebral infarction;

(4) a method of (2), wherein the disease is a traumatic brain edema or a traumatic intracranial hemorrhage;

(5) a method of (1), wherein
A is (i) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group or (ii) —Y=R$^4$ in which —Y= is —N= or —NHN= and R$^4$ is an optionally substituted divalent hydrocarbon group, R$^1$ is (i) a hydrogen atom, or (ii) —Z—R$^5$ in which —Z— is —O—, —S— or —NH—, and R$^5$ is a hydrogen atom, an optionally substituted hydrocarbon group or an optionally substituted aromatic heterocyclic group, R$^2$ is a hydrogen atom, a halogen atom or an optionally substituted hydrocarbon group, and D and E are independently a hydrogen atom, an amino group, an azido group, a halogen atom or an optionally protected hydroxyl group;

(6) a method of (1) or (5), wherein the substituent which the divalent hydrocarbon group may optionally have is a substituted amino group, an optionally substituted aryl group, or an optionally substituted aromatic heterocyclic group;

(7) a method of (1) or (5), wherein —X— is —NH— or —NHNH—, and R$^3$ is (1) a hydrogen atom, (ii) an acyl group, (iii) an optionally substituted C$_{1-6}$ alkyl group, (iv) an optionally substituted C$_{6-14}$ aryl group or (v) an optionally substituted 5- to 14-membered monocyclic or condensed polycyclic aromatic heterocyclic group;

(8) a method of (1) or (5), wherein R$^4$ is a divalent lower aliphatic hydrocarbon group optionally having one substituent selected from the group consisting of (i) a mono- or di-C$_{1-6}$alkylamino group, (ii) an optionally substituted C$_{6-4}$aryl group and (iii) an optionally substituted 5- to 14-membered monocyclic or condensed polycyclic aromatic heterocyclic group;

(9) a method of (1) or (5), wherein A is —NHNH—R$^{3\ a}$ in which R$^{3\ a}$ is a 5- to 14-membered monocyclic or condensed polycyclic aromatic heterocyclic group optionally having one to three substituents selected from the group consisting of amino, mono-C$_{1-6}$alkylamino, di-C$_{1-6}$alkylamino, anilino, halogen, cyano, hydroxyl, C$_{1-6}$alkyl, C$_{1-6}$alkoxy, C$_{1-6}$alkyl-carbonyl, carbamoyl, mono-C$_{1-6}$alkylcarbamoyl, di-C$_{1-6}$alkylcarbamoyl, mono- or di-C$_{6-14}$arylcarbamoyl and phenyl;

(10) a method of (1) or (5), wherein A is —NH$_2$;

(11) a method of (1) or (5), wherein —Z— is —O— or —NH—, and R$^5$ is (i) an optionally substituted C$_{1-6}$alkyl group, (ii) an optionally substituted C$_{6-14}$aryl group or (iii) an optionally substituted 5- to 14-membered monocyclic or condensed polycyclic aromatic heterocyclic group;

(12) a method of (1) or (5), wherein R$^1$ is a hydrogen atom;

(13) a method of (1) or (5), wherein —NH—R$^{5\ a}$ in which R$^{5\ a}$ is a C$_{6-14}$ aryl group optionally having one to three substituents selected from the group consisting of amino, mono-C$_{1-6}$alkylamino, di-C$_{1-6}$alkylamino, anilino, halogen, cyano, hydroxyl, C$_{1-6}$alkyl, C$_{1-6}$alkoxy, C$_{1-6}$alkyl-carbonyl, 5- or 6-membered heterocycle-carbonyl, carbamoyl, mono-C$_{1-6}$alkylcarbamoyl, di-C$_{1-6}$alkylcarbamoyl and mono- or di- C$_{6-14}$arylcarbamoyl;

(14) a method of (1) or (5), wherein R$^2$ is a hydrogen atom;

(15) a method of (1) or (5), wherein R$^6$ is a hydroxyl group, a C$_{6-14}$ aryl-carbonyloxy group, a C$_{1-6}$alkylthio group, an amino group, a mono-C$_{1-6}$alkylamino group, a di-C$_{1-6}$alkylamino group or an anilino group;

(16) a method of (1) or (5), wherein W is >C=O, and R$^6$ is a mono- or di-C$_{1-6}$alkylamino group;

(17) a method of (1) or (5), wherein B is —CH$_2$OH;

(18) a method of (1) or (5), wherein D and E are independently an optionally protected hydroxyl group;

(19) a method of (18), wherein the protective group of an optionally protected hydroxyl group is formyl, C$_{1-6}$alkyl-carbonyl, benzoyl, nicotinoyl, C$_{1-6}$alkyl, benzyl, C$_{3-6}$cycloalkyl-carbonyl, 2',3'-O-(C$_{1-6}$alkylidene), 2',3'-O-(C$_{1-6}$alkoxy-C$_{1-6}$alkylidene) or 2',3'-O-(C$_{4-7}$cycloalkylidene);

(20) a method of (18), wherein the protective group of an optionally protected hydroxyl group is 2',3'-O-(C$_{1-6}$alkoxy-C$_{1-6}$alkylidene);

(21) a method of (1) or (5), wherein D and E are hydroxyl groups;

(22) a method of (1), wherein

A is —NHNH—R$^{3\ b}$ in which R$^{3\ b}$ is a 5- to 14-membered monocyclic or condensed polycyclic aromatic heterocyclic group optionally having one to three substituents selected from the group consisting of a C$_{1-6}$ alkyl group, an amino group and a phenyl group, R$^1$ and R$^2$ are hydrogen atoms, B is —CH$_2$ OH, and D and E are independently an optionally protected hydroxyl group;

(23) a method of (1), wherein

A is —NH$_2$,

R$^1$ and R$^2$ are hydrogen atoms,

B is of the following:

wherein R$^{7\ a}$ and R$^{8\ a}$ are independently (i) a hydrogen atom, (ii) a C$_{1-6}$alkyl group, (iii) a formyl group, (iv) a C$_{1-6}$alkyl-carbonyl group, (v) a C$_{7-16}$aralkyl-carbonyl group or (vi) a nicotinoyl group, or R$^{7\ a}$ and R$^{6\ a}$ taken together with the adjacent nitrogen atom form a 5- or 6-membered nitrogen-containing heterocyclic group, and D and E are independently an optionally protected hydroxyl group;

(24) a method of (22) or (23), wherein D and E are hydroxyl groups;

(25) a method of (1), wherein the compound (I) is one of the formula:

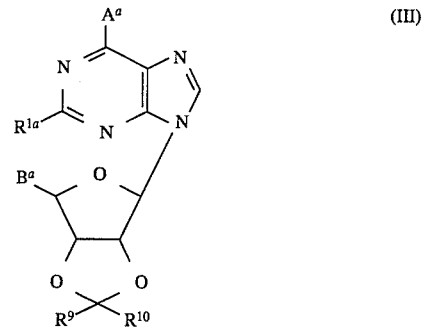

wherein
- $A^a$ is (i) —$NH_2$ or (ii) —NHNH—$R^{3\ b}$ in which $R^{3\ b}$ is a 5- to 14-membered monocyclic or condensed polycyclic aromatic heterocyclic group optionally having one to three substituents selected from the group consisting of a $C_{1-6}$alkyl group, an amino group and a phenyl group,
- $R^{1\ a}$ is (i) a hydrogen atom or (ii) —NH—$R^{5\ a}$ in which $R^{5\ a}$ is a $C_{6-14}$aryl group optionally having one to three substituents selected from the group consisting of amino, mono-$C_{1-6}$alkylamino, di-$C_{1-6}$alkylamino, anilino, halogen, cyano, hydroxyl, $C_{1-6}$alkyl, $C_{1-6}$alkoxy, $C_{1-6}$alkyl-carbonyl, 5- or 6-membered heterocycle-carbonyl, carbamoyl, mono-$C_{1-6}$alkylcarbamoyl, di-$C_{1-6}$alkylcarbamoyl and mono- or di-$C_{6-14}$arylcarbamoyl,
- $B^a$ is —CO—$R^{6\ a}$ in which $R^{6\ a}$ is a mono- or di-$C_{1-6}$alkylamino group, and
- $R^9$ and $R^{10}$ are independently a hydrogen atom, a $C_{1-6}$alkyl group or a $C_{1-6}$alkoxy group;

(26) a method of (1), wherein the compound (I) is 6-[2-(9H-purine-6-yl)hydrazino]nebularine;

(27) a method of (1), wherein the compound (I) is 6-[2-(4-amino-s-triazin-2-yl)hydrazino]nebularine;

(28) a method of (1), wherein the compound (I) is 2-[p-(morpholinocarbonyl)anilino]adenosine; and

(29) a method of (1), wherein the comound (I) is 2'-3'-O-(1-ethoxyethylidene)adenosine-5'-(N-ethylcarboxamide).

The term "halogen atom" used in the present specification represents fluorine, chlorine, bromine, iodine and so on.

The term "acyl group" used in the present specification represents an acyl group derived from carboxylic acid, such as formyl, $C_{1-6}$alkyl-carbonyl (e.g. acetyl, propionyl and butyryl), $C_{3-6}$cycloalkylcarbonyl (e.g. cyclopropylcarbonyl, cyclobutylcarbonyl, cyclopentylcarbonyl and cyclohexylcarbonyl), $C_{6-14}$aryl-carbonyl (e.g. benzoyl) and nicotinoyl.

Such $C_{1-6}$alkyl-carbonyl, $C_{3-6}$cycloalkyl-carbonyl, $C_{6-14}$aryl-carbonyl and nicotinoyl may optionally have one to three substituents selected from among $C_{1-6}$alkoxy (e.g. methoxy, ethoxy, propoxy and isopropoxy), hydroxyl, amino, nitro, and a halogen atom (e.g. fluorine, chlorine, bromine and iodine), etc. at the substitutable positions. Here, in the case of two or more substituents, they may be either identical or different.

The "hydrocarbon group" of the term "an optionally substituted hydrocarbon group" used in the present specification represents as follows;

(1) acyclic hydrocarbon group:
a) $C_{1-6}$alkyl group (e.g. methyl, ethyl, propyl, isopropyl, butyl, isobutyl, sec-butyl and tert-butyl),
b) $C_{2-6}$alkenyl group (e.g. vinyl, allyl, isopropenyl, butenyl, isobutenyl and sec-butenyl), and
c) $C_{2-6}$alkynyl (e.g. propargyl, ethynyl, butynyl and 1-hexynyl), and (2) cyclic hydrocarbon group:
a) $C_{3-6}$cycloalkyl group (e.g. cyclopropyl, cyclobutyl, cyclopentyl and cyclohexyl),
b) $C_{6-14}$aryl group (e.g. phenyl, tolyl, xylyl, 1-naphthyl, 2-naphthyl, biphenyl, 2-indenyl and 2-anthryl), and
c) $C_{7-16}$aralkyl group (e.g. benzyl, phenethyl, diphenylmethyl, triphenylmethyl, 1-naphthylmethyl, 2-naphthylmethyl, 2-diphenylethyl, 3-phenylpropyl, 4-phenylbutyl and 5-phenylpentyl).

The "hydrocarbon group" may optionally have one to five, preferably one to three substituents selected from among amino, nitro, mono-$C_{1-6}$alkylamino (e.g. methylamino and ethylamino), di-$C_{1-6}$alkylamino (e.g. dimethylamino and diethylamino), anilino, a halogen atom (e.g. fluorine, chlorine, bromine and iodine), sulfo, cyano, hydroxyl, $C_{1-6}$alkyl (e.g. methyl, ethyl, propyl, isopropyl, butyl, isobutyl, sec-butyl and tert-butyl), $C_{1-6}$alkoxy (e.g. methoxy, ethoxy, propoxy and isopropoxy), oxo, carboxyl, $C_{1-6}$alkoxy-carbonyl (e.g. methoxycarbonyl, ethoxycarbonyl, propoxycarbonyl, isopropoxycarbonyl and butoxycarbonyl), formyl, $C_{1-6}$alkylcarbonyl (e.g. acetyl and propionyl), $C_{3-6}$cycloalkylcarbonyl (e.g. cyclopropylcarbonyl, cyclobutylcarbonyl, cyclopentylcarbonyl and cyclohexylcarbonyl), 5- or 6-membered heterocycle-carbonyl(e.g.4-morpholinocarbonyl, 1-pyrrolidinylcarbonyl, piperidinocarbonyl and nicotinoyl), carbamoyl, mono-$C_{1-6}$alkylcarbamoyl (e.g. methylcarbamoyl and ethylcarbamoyl), di-$C_{1-6}$alkylcarbamoyl (e.g. dimethylcarbamoyl and diethylcarbamoyl), $C_{6-14}$aryl-carbamoyl (e.g. phenylcarbamoyl, 1-naphthylcarbamoyl, 2-naphthylcarbamoyl and tolylcarbamoyl) and mercapto.

These substituents may be located on any substitutable position on the hydrocarbon group, and in the case of two or more substituents, they may be either identical or different.

Besides, the "hydrocarbon group" may be optionally substituted by a heterocyclic group optionally having one substituent (such as those shown below) or an aryl group optionally having one substituent (such as those shown below) and so on.

The "aromatic heterocyclic group" in the term "an optionally substituted aromatic heterocyclic group" used in the present specification represents a 5- to 14-membered monocyclic aromatic heterocyclic group or condensed polycyclic aromatic heterocyclic group having preferably one to four hetero atoms of one or two sorts selected from a nitrogen atom, an oxygen atom and a sulfur atom besides a carbon atom.

As the "5- to 14-membered monocyclic or condensed polycyclic aromatic heterocyclic group", 1-pyrrolyl, 2-pyrrolyl, 3-pyrrolyl, 2-imidazolyl, 4-imidazolyl, 2-thienyl, 3-thienyl, 3-furyl, 3-isothiazolyl, 3-isooxazolyl, 2-pyridyl, 3-pyridyl, 4-pyridyl, 2-pyrimidinyl, 4-pyrimidinyl, 5-pyrimidinyl, 2-pyrazinyl, 3-pyrazinyl, 3-pyridazinyl, 4-pyridazinyl, s-triazin-2-yl, 1,2,4-triazin-3-yl, 1,2,4-triazin-5-yl, 9H-purin-6-yl, 2-quinolyl, 3-quinolyl, 4-quinolyl, 1-isoquinolyl, 3-isoquinolyl, 4-isoquinolyl, 1-indolyl, 2-indolyl, 3-indolyl, 1-indazolyl, 1H-3-indazolyl, 1-benzimidazolyl, 1H-2-benzimidazolyl and 1-benzotriazolyl are exemplified.

Preferably, a 5- to 10-membered monocyclic or condensed bicyclic aromatic heterocyclic group containing one to four nitrogen atoms besides carbon atoms, such as 1-pyrrolyl, 2-pyrrolyl, 3-pyrrolyl, 2-imidazolyl, 4-imidazolyl, 2-pyridyl, 3-pyridyl, 4-pyridyl, 2-pyrimidinyl, 4-pyrimidinyl, 5-pyrimidinyl, 2-pyrazinyl, 3-pyrazinyl, 3-pyridazinyl, 4-pyridazinyl, s-triazin-2-yl, 1,2,4-triazin-3-yl, 1,2,4-triazin-5-yl, 9H-purin-6-yl, 2-quinolyl, 3-quinolyl, 4-quinolyl, 1-isoquinolyl, 3-isoquinolyl, 4-isoquinolyl, 1-indolyl, 2-indolyl, 3-indolyl, 1-indazolyl, 1H-3-indazolyl, 1-benzimidazolyl, 1H-2-benzimidazolyl and 1-benzotriazolyl, is widely used.

As the substituents which the "aromatic heterocyclic group" may optionally have, for example, the same substituents as the "hydrocarbon group" may optionally have are used.

These substituents may be located on any substitutable position on the aromatic heterocyclic group and the number of substituents is one to three. Here, in the case of two or more substituents, they may be either identical or different.

The term "divalent hydrocarbon group" used in the present specification represents a group obtained by removing two hydrogen atoms from a hydrocarbon, preferably a group obtained by removing two hydrogen atoms from the same carbon atom. As such a divalent hydrocarbon group, $C_{1-6}$alkylidene group such as methylene and ethylidene, a divalent lower aliphatic hydrocarbon group such as vinylidene, $C_{1-6}$alkenylidene, etc. are used. Among others, concretely, for example, $=CH_2$, $=CHCH_3$,

$=CHCH_2CH_3$,

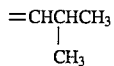

and $=CHCH_2CH_2CH_3$ are preferable.

The "divalent hydrocarbon group" may be optionally substituted by substituents selected from among a substituted amino group (such as those shown below), an optionally substituted aryl group (such as those shown below), and an optionally substituted aromatic heterocyclic group (such as those shown above), etc., and one substituent is usually preferable.

These substituents may be located on any substitutable position on the divalent hydrocarbon group.

The above "substituted amino group" represents an amino group having one or two substituents selected from among a $C_{1-6}$alkyl group (e.g. methyl, ethyl, propyl, isopropyl, butyl, isobutyl, sec-butyl and tert-butyl), a $C_{1-6}$alkoxy group (e.g. methoxy, ethoxy, propoxy and isopropoxy), a $C_{6-14}$ aryl group (e.g. phenyl, tolyl, xylyl, 1-naphthyl, 2-naphthyl, biphenyl, 2-indenyl and 2-anthryl, especially phenyl, 1-naphthyl and 2-naphthyl), an acyl group (e.g. the same as those shown above) and a halogen atom (e.g. fluorine, chlorine, bromine and iodine).

The "aryl group" in the term "an optionally substituted aryl group" used in the present specification represents, for example, a $C_{6-14}$aryl group such as phenyl, tolyl, xylyl, 1-naphthyl, 2-naphthyl, biphenyl, 2-indenyl and 2-anthryl, and especially phenyl, 1-naphthyl, 2-naphthyl and so on are widely used.

The "aryl group" may optionally have one to three substituents selected from among amino, nitro, mono-$C_{1-6}$alkylamino (e.g. methylamino and ethylamino), di-$C_{1-6}$alkylamino (e.g. dimethylamino and diethylamino), anilino, a halogen atom (e.g. fluorine, chlorine, bromine and iodine), sulfo, cyano, hydroxyl, $C_{1-6}$alkyl (e.g. methyl, ethyl, propyl, isopropyl, butyl, isobutyl, sec-butyl and tert-butyl), $C_{1-6}$alkoxy (e.g. methoxy, ethoxy, propoxy and isopropoxy), oxo, carboxyl, $C_{1-6}$ alkoxy-carbonyl (e.g. methoxycarbonyl, ethoxycarbonyl, propoxycarbonyl, isopropoxycarbonyl and butoxycarbonyl), $C_{1-5}$acyl (e.g. formyl, acetyl and propionyl), 5- or 6-membered heterocycle-carbonyl (e.g. 4-morphorinocarbonyl, 1-pyrrolidinylcarbonyl, piperidinocarbonyl and nicotinoyl, especially 4-morphorinocarbonyl) and mercapto.

These substituents may be located on any substitutable position on the aryl group and in the case of two or more substituents, they may be either identical or different.

The "heterocyclic group" in the term "an optionally substituted heterocyclic group" used in the present specification represents, for example, a 5- to 14-membered monocyclic- or condensed polycyclic heterocyclic group containing preferably one to four hetero atoms of one or two sorts selected from a nitrogen atom, an oxygen atom and a sulfur atom besides a carbon atom.

Concretely, a 5- to 14-membered monocyclic aromatic heterocyclic group or condensed polycyclic aromatic heterocyclic group such as 1-pyrrolyl, 2-pyrrolyl, 3-pyrrolyl, 2-imidazolyl, 4-imidazolyl, 2-thienyl, 3-thienyl, 3-furyl, 3-isothiazolyl, 3-isooxazolyl, 2-pyridyl, 3-pyridyl, 4-pyridyl, 2-pyrimidinyl, 4-pyrimidinyl, 5-pyrimidinyl, 2-pyrazinyl, 3-pyrazinyl, 3-pyridazinyl, 4-pyridazinyl, s-triazin-2-yl, 1,2,4-triazin-3-yl, 1,2,4-triazin-5-yl, 9H-purin-6-yl, 2-quinolyl, 3-quinolyl, 4-quinolyl, 1-isoquinolyl, 3-isoquinolyl, 4-isoquinolyl, 1-indolyl, 2-indolyl, 3-indolyl, 1-indazolyl, 1H-3-indazolyl, 1-benzimidazolyl, 1H-2-benzimidazolyl and 1-benzotriazolyl, and a 5- to 14-membered monocyclic non-aromatic heterocyclic group or condensed polycyclic non-aromatic heterocyclic group such as 1-pyrrolidinyl, 2-pyrrolidinyl, 3-pyrrolidinyl, 1-imidazolidinyl, 2-imidazolidinyl, 4-imidazolidinyl, 1-pyrazolidinyl, 2-pyrazolidinyl, 3-pyrazolidinyl, 1-piperidyl, 2-piperidyl, 3-piperidyl, 4-piperidyl, 1-piperazinyl, 2-piperazinyl, 3-piperazinyl, 2-morpholinyl, 3-morpholinyl, 4-morpholinyl, 2-thiomorpholinyl, 3-thiomorpholinyl, 4-thiomorpholinyl, 1H-hexahydroazepin-1-yl, 1H-hexahydroazepin-2-yl, 1H-hexahydroazepin-3-yl, 1H-hexahydroazepine-4-yl, 2-oxazolidinyl, 2-thiazolidinyl, 1-indolinyl, 2-indolinyl, 3-indolinyl, 1-isoindolinyl, 2-isoindolinyl, 2,3,4,5-tetrahydrobenzazepin-1-yl and 1,2,4,5-tetrahydrobenzazepin-3-yl, are exemplified.

Preferably, for example, a 5- to 10-membered monocyclic or condensed bicyclic aromatic heterocyclic group containing one to four nitrogen atoms besides carbon atoms, such as 1-pyrrolyl, 2-pyrrolyl, 3-pyrrolyl, 2-imidazolyl, 4-imidazolyl, 2-pyridyl, 3-pyridyl, 4-pyridyl, 2-pyrimidinyl, 4-pyrimidinyl, 5-pyrimidinyl, 2-pyrazinyl, 3-pyrazinyl, 3-pyridazinyl, 4-pyridazinyl, s-triazin-2-yl, 1,2,4-triazin-3-yl, 1,2,4-triazin-5-yl, 9H-purin-6-yl, 2-quinolyl, 3-quinolyl, 4-quinolyl, 1-isoquinoyl, 3-isoquinolyl, 4-isoquinolyl, 1-indolyl, 2-indolyl, 3-indolyl, 1-indazolyl, 1H-3-indazolyl, 1-benzimidazolyl, 1H-2-benzimidazolyl, 1-benzotriazolyl, 1-pyrrolidinyl, 2-pyrrolidinyl, 3-pyrrolidinyl, 1-imidazolidinyl, 2-imidazolidinyl, 4-imidazolidinyl, 1-pyrazolidinyl, 2-pyrazolidinyl, 3-pyrazolidinyl, 1-piperidyl, 2-piperidyl, 3-piperidyl, 4-piperidyl, 1-piperazinyl, 2-piperazinyl, 3-piperazinyl, 1H-hexahydroazepin-1-yl, 1H-hexahydroazepin-2-yl, 1H-hexahydroazepin-3-yl, 1H-hexahydroazepin-4-yl, 1-indolinyl, 2-indolinyl, 3-indolinyl, 1-isoindolinyl, 2-isoindolinyl, 2,3,4,5-tetrahydrobenzazepin-1-yl and 1,2,4,5-tetrahydrobenzazepin-3-yl, is widely used.

As the substituents which the "heterocyclic group" may optionally have, the same substituents as the "hydrocarbon group" may optionally have are used.

These substituents may be located on any substitutable position on the heterocyclic group, and the number of substituents is one to three. Here, in the case of two or more substituents, they may be either identical or different.

The "alkoxy group" in the term "an optionally substituted alkoxy group" used in the present specification represents a $C_{1-6}$alkoxy group (e.g. methoxy, ethoxy, propoxy and isopropoxy) and so on.

The "acyloxy group" in the term "an optionally substituted acyloxy group" used in the present specification represents a $C_{1-6}$alkyl-carbonyloxy group (e.g. methylcarbonyloxy and ethylcarbonyloxy), a $C_{3-6}$cycloalkyl-carbonyloxy group (e.g. cyclopropylcarbonyloxy and cyclobutylcarbonyloxy), a $C_{6-14}$aryl-carbonyloxy group (e.g. benzoyloxy), nicotinoyloxy and so on.

The "alkylsulfinyl group" in the term "an optionally substituted alkylsulfinyl group" used in the present specification represents a $C_{1-6}$alkylsulfinyl group (e.g. methylsulfinyl, ethylsulfinyl, propylsulfinyl and isopropylsulfinyl) and so on.

The team "alkylsulfonyl group" in the term "an optionally substituted alkylsulfonyl group" used in the present specification represents a $C_{1-6}$alkylsulfonyl group (e.g. methanesulfonyl, ethanesulfonyl, propanesulfonyl and isopropanesulfonyl) and so on.

As the substituents which the "alkoxy group", "acyloxy group", "alkylsulfinyl group" and "alkylsulfonyl group" may optionally have, for example, the same substituents as the "hydrocarbon group" may optionally have are used.

These substituents may be located on any substitutable position. Here, in the case of two or more substituents, they may be either identical or differnt.

As the substituents which the "O-phosphono group" may optionally have, for example, $C_{1-6}$alkyl (e.g. methyl, ethyl, propyl, isopropyl, butyl, isobutyl, sec-butyl, tert-butyl) are used.

The term "optionally substituted amino group" used in the present specification represents:

wherein $R^7$ and $R^8$ are independently a hydrogen atom, an acyl group or an optionally substituted hydrocarbon group, or $R^7$ and $R^8$ taken together with their adjacent nitrogen atom to form a 5- or 6-membered nitrogen-containing heterocyclic group.

As the "nitrogen-containing heterocyclic group formed with the adjacent nitrogen atom", a 5- or 7-membered nitrogen-containing heterocyclic group optionally having one to three atoms selected from among a nitrogen atom, an oxygen atom and a sulfur atom besides a carbon atom such as:

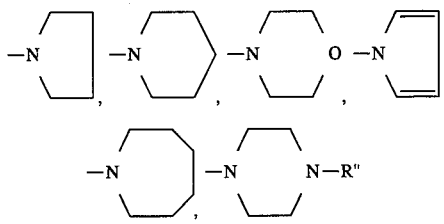

in which $R^{11}$ is a hydrogen atom or an optionally substituted hydrocarbon group, is used.

These nitrogen-containing heterocyclic group may optionally have, for example, the same substituents as the "hydrocarbon group" may optionally have.

These substituents may be located on any substitutable position on the nitrogen-containing heterocyclic group formed with the adjacent nitrogen atom, and the number of substituents is one to three. Here, in the case of two or more substituents, they may be either identical or different.

The "protective group" in the term "optionally protected hydroxyl group" used in the present specification represents a protective group generally used in the field of sugar and so on. When both D and E are hydroxyl groups, they may be optionally protected at the same time. Concretely, formyl, $C_{1-6}$alkyl-carbonyl (e.g. acetyl, propionyl and butyryl), $C_{3-6}$cycloalkylcarbonyl (e.g. cyclopropylcarbonyl, cyclobutylcarbonyl and cyclopentylcarbonyl), $C_{6-14}$aryl-carbonyl (e.g. benzoyl), $C_{7-16}$aralkyl (e.g. benzyl, phenethyl, 1-naphthylmethyl and 2-naphthylmethyl), nicotinoyl, $C_{1-6}$alkyl (e.g. methyl, ethyl, propyl, isopropyl, butyl, isobutyl, sec-butyl and tert-butyl), $C_{1-6}$alkylidene (e.g. methylidene, ethylidene and propylidene), $C_{1-4}$alkoxy-$C_{1-6}$ alkylidene (e.g. methoxymethylidene, ethoxymethylidene, 1-methoxyethylidene and 1-ethoxyethylidene), $C_{4-7}$cycloalkylidene (e.g. cyclopentylidene and cyclohexylidene) and so on are widely used.

In the above formula, A is (i) a halogen atom, (ii) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group or (iii) —Y=$R^4$ in which —Y= is —N= or —NHN= and $R^4$ is an optionally substituted divalent hydrocarbon group.

As preferred examples of A, (i) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group or (ii) —Y=$R^4$ in which —Y= is —N= or —NHN= and $R^4$ is an optionally substituted divalent hydrocarbon group, is used.

In the above formula, $R^1$ is (i) a hydrogen atom, (ii) a halogen atom, (iii) an optionally substituted hydrocarbon group, (iv) an optionally substituted heterocyclic group or (v) —Z—$R^5$ in which —Z— is —O—, —S— or —NH— and $R^5$ is a hydrogen atom, an optionally substituted hydrocarbon group or an optionally subsituted aromatic heterocyclic group.

As preferred examples of $R^1$, (i) a hydrogen atom or (ii) —Z—$R^5$ in which —Z— is —O—, —S— or —NH— and $R^5$ is a hydrogen atom, an optionally substituted hydrocarbon group or an optionally substituted aromatic heterocyclic group, is widely used.

In the above formula, $R^2$ is a hydrogen atom, a halogen atom, an optionally substituted hydrocarbon group or an optionally substituted heterocyclic group.

As preferred examples of $R^2$, a hydrogen atom, a halogen atom or an optionally substituted hydrocarbon group is widely used.

In the above formula, B is —W—$R^6$ in which —W— is —$CH_2$—, >C=O or >C=S and $R^6$ is hydroxyl, or an optionally substituted alkoxy, acyloxy, alkylsulfinyl, alkylsulfonyl, O-phosphono or amino group, or B together with E may optionally form a cyclic phosphoric ester.

In the above formula, D and E are independently a hydrogen atom, an optionally substituted amino group, an azido group, a halogen atom or an optionally protected hydroxyl group.

As preferred examples of D and E, a hydrogen atom, an amino group, an azido group, a halogen atom or an optionally protected hydroxyl group is independently used widely.

—X— is preferably —NH— or —NHNH—, etc.

$R^3$ is preferably (1) a hydrogen atom, (ii) an acyl group, (ill) an optionally substituted $C_{1-6}$alkyl group, (iv) an optionally substituted $C_{6-14}$aryl group or (v) an optionally substituted 5- to 14-membered monocyclic or condensed polycyclic aromatic heterocyclic group, etc.

—Y= is preferably —NH= and so on.

$R^4$ is preferably a divalent lower aliphatic hydrocarbon group optionally having one substituent selected from the group consisting of (i) a mono- or di-$C_{1-6}$alkylamino group, (ii) an optionally substituted $C_{6-14}$aryl group and (iii) an optionally substituted 5- to 14-membered monocyclic or condensed polycyclic aromatic heterocyclic group, and so on.

A is preferably —NHNH—$R^{3\ a}$ in which $R^{3\ a}$ is a 5- to 14-membered monocyclic or condensed polycyclic aromatic heterocyclic group optionally having one to three substituents selected from the group consisting of amino, mono-$C_{1-6}$alkylamino, di-$C_{1-6}$alkylamino, anilino, halogen, cyano, hydroxyl, $C_{1-6}$alkyl, $C_{1-6}$alkoxy, $C_{1-6}$alkyl-carbonyl, carbamoyl, $C_{1-6}$alkylcarbamoyl, mono- or di-$C_{6-14}$arylcarbamoyl and phenyl, and so on.

Besides, A is also preferably —$NH_2$—.

—Z— is preferably —O— or —NH—, etc. and especially —NH— is widely used.

$R^5$ is preferably (i) an optionally substituted $C_{1-6}$alkyl group, (ii) an optionally substituted $C_{6-14}$aryl group or (iii) an optionally substituted 5- to 14-membered monocyclic or condensed polycyclic aromatic heterocyclic group, etc.

$R^1$ is preferably a hydrogen atom. And as an example of $R^1$, —NH—$R^{5\ a}$ in which $R^{5\ a}$ is a $C_{6-14}$aryl group optionally having one to three substituents selected from the group consisting of amino, mono-$C_{1-6}$alkylamino, di-$C_{1-6}$ alkylamino, anilino, halogen, cyano, hydroxyl, $C_{1-6}$alkyl, $C_{1-6}$alkoxy, $C_{1-6}$alkyl-carbonyl, 5- or 6-membered heterocycle-carbonyl, carbamoyl, mono-$C_{1-6}$alkylcarbamoyl, di-$C_{1-6}$alkylcarbamoyl and mono- or di-$C_{6-14}$arylcarbamoyl, is widely used.

$R^2$ is preferably a hydrogen atom or a halogen atom, etc. and especially a hydrogen atom and so on is widely used.

W is preferably —$CH_2$— or >C=O, etc.

$R^6$ is preferably a hydroxyl group, a $C_{6-14}$ aryl-carbonyloxy group, a $C_{1-6}$alkylsulfinyl group, an amino group, a mono-$C_{1-6}$alkylamino group, a di-$C_{1-6}$alkylamino group or an anilino group, etc. and especially a hydroxyl group, a $C_{1-6}$alkylsulfinyl group, a mono-$C_{1-6}$alkylamino group or a di-$C_{1-6}$alkylamino group, etc. is widely used.

When W is >C=O, a mono- or di-$C_{1-6}$alkylamino group, etc. is widely used as $R^6$.

B is preferably —$CH_2OH$ and so on.

D and E are preferably an optionally protected hydroxyl group and so on. As a protective group of an optionally protected hydroxyl group, formyl, $C_{1-6}$alkyl-carbonyl, benzoyl, nicotinoyl, $C_{1-6}$alkyl, benzyl, $C_{3-6}$cycloalkyl-carbonyl, 2',3'-O-($C_{1-6}$alkylidene), 2',3'-O-($C_{1-6}$alkoxy-$C_{1-6}$alkylidene) or 2',3'-O-($C_{4-7}$cycloalkylidene), etc. is widely used.

As D and E, for example, a hydroxyl group is widely used.

Preferred examples of a compound (I) or a pharmaceutically acceptable salt thereof are:

(1) that of the above formula (I), wherein

A is —NHNH—$R^{3\ b}$ in which $R^{3\ b}$ is a 5- to 14-membered monocyclic or condensed polycyclic aromatic heterocyclic group optionally having one to three substituents selected from the group consisting of a $C_{1-6}$alkyl group, an group and a phenyl group, $R^1$ and $R^2$ are hydrogen atoms, B is —$CH_2OH$, and D and E are independently an optionally protected hydroxyl group;

(2) that of the above formula (I), wherein

A is —$NH_2$, $R^1$ and $R^2$ are hydrogen atoms,

B is of the following:

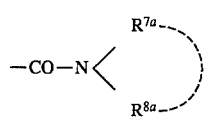 (II)

wherein $R^{7\ a}$ and $R^{8\ a}$ are independently (i) a hydrogen atom, (ii) a $C_{1-6}$alkyl group, (iii) a formyl group, (iv) a $C_{1-6}$alkyl-carbonyl group, (v) a $C_{6-14}$aryl-carbonyl group or (vi) a nicotinoyl group, or $R^{7\ a}$ and $R^{8\ a}$ taken together with the adjacent nitrogen atom form a 5-or 6-membered nitrogen-containing heterocyclic group, and D and E are independently an optionally protected hydroxyl group; or (3) that of the formula:

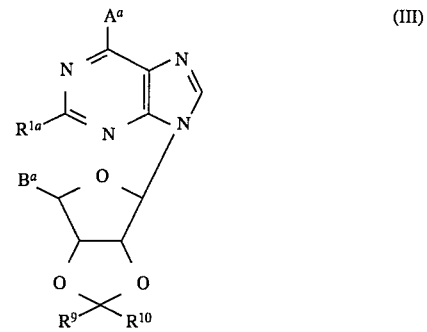 (III)

wherein $A^a$ is (i) —NH, or (ii) —NHNH—$R^{3\ b}$ in which $R^{3\ b}$ is a 5- to 14-membered monocyclic or condensed polycyclic aromatic heterocyclic group optionally having one to three substituents selected from the group consisting of a $C_{1-6}$alkyl group, an amino group and a phenyl group, $R^{1\ a}$ is (i) a hydrogen atom or (ii) —NH—$R^{5\ a}$ in which $R^{5\ a}$ is a $C_{6-14}$aryl group optionally having one to three substituents selected from the group consisting of amino, mono-$C_{1-6}$alkylamino, di-$C_{1-6}$alkylamino, anilino, halogen, cyano, hydroxyl, $C_{1-6}$alkyl, $C_{1-6}$alkoxy, $C_{1-6}$alkyl-carbonyl, 5- or 6-membered heterocycle-carbonyl, carbamoyl, mono-$C_{1-6}$alkylcarbamoyl, di-$C_{1-6}$alkylcarbamoyl and mono- or di-$C_{6-14}$arylcarbamoyl, $B^a$ is —CO—$R^{6\ a}$ in which $R^{6\ a}$ is a mono- or di-$C_{1-6}$alkylamino group, and $R^9$ and $R^{10}$ are independently a hydrogen atom, a $C_{1-6}$alkyl group or a $C_{1-6}$alkoxy group.

A compound (I) or a pharmaceutically acceptable salt thereof used in the present invention can be produced by the methods or their equivalents described in U.S. Pat. No. 3,819,613, U.S. Pat. No. 4,255,565, U.S. Pat. No. 4,225,591, U.S. Pat. No. 4,341,769 and JP-A-58 83698, DE-2632951, DE-2941592, "Annalen der Chemie, Justus Liebigs, vol. 656, p. 158, (1962)" "Biochimica et Biophysica Acta, vol. 65, p. 558, (1962 )" "Journal of American Chemical Society, vol. 86, p. 1242, (1964)" "Chemische Berichte, vol. 98, p.1699, (1965)" "Takeda Laboratory Bulletin, vol. 44, p. 220, (1985)" "Chemical and Pharmaceutical Bulletin, vol. 23, p. 795, (1975 )" "Chemistry of Nucleosides and Nucleotides, vols. 1 and 2, (1988)" "Nucleic Acids in Chemistry and Biology, (1990)" "Chemistry of Nucleic Acids, Yoshihisa Mizuno, Asakura Shoten, (1974)" and so on.

As a pharmaceutically acceptable salt of a compound (I) in the present invention, medically permissible acid addition salts is preferable. As such salts, salts with inorganic acids, such as hydrochloride, hydrobromic acid salt, hydroiodic acid salt, sulfate and phosphate, and salts with organic acids, such as acetate, oxalate, succinic acid salt, ascorbic acid salt, maleate, lactate, citric acid salt, tartrate, methanesulfonic acid salt and benzoate, and salts of alkali metals (e.g. potassium and sodium), ammonia, etc. are used.

The medicament for inhibiting a vascular permeability enhancer according to the present invention is produced by using a compound (I) or its salt as it is or mixed with a medically permissible carrier, in the well-known way, for example, as a tablet (including a sugar-coating tablet and a film-coating tablet), a powder, a granule, a capsule (including a microcapsule and a soft elastic capsule), a liquid medicine, an injection, a suppository and a sustained release drug.

The content of the compound (I) or its salt in the medicament according to the present invention is usually about 0.1 to 100 wt % of the whole medicament. The medicament in the present invention is prepared according to the way described in the Japanese Pharmacopoeia and so on. For example, a tablet can be produced by granulating a medicament as it is or uniformly mixed with an excipient vehicle, a bonding agent, a disintegrator or other appropriate additives, in an appropriate way, and then adding a lubricant, etc. and compression-molding it, or by directly compression-molding the medicament as it is or uniformly mixed with an excipient vehicle, a bonding agent, a disintegrator or other appropriate additives. And a coloring agent, sweetener and so on can be added to the present medicament as occassion arises. Furthermore, coating can be applied to the present medicament with an appropriate coating agent. For example, an injection can be produced by dissolving, suspending or emulsifying a prescribed quantity of a medicament in an injection solution, a physiological saline solution, a Ringer's solution, etc. in the case of an aqueous solvent, and usually in a vegetable oil, etc. in the case of a nonaqueous solvent, so as to obtain a prescribed quantity of an injection, or by sealing up a prescribed quantity of a medicament in a container for an injection.

As a medically permissible carrier, every conventional kind of an organic or inorganic carrier material for a medicine material is used, and mixed as an excipient vehicle, a lubricant, a bonding agent or a disintegrator in a solid medicine, or as a solvent, a solubilizer, a suspending agent, an isotonizing agent, a buffer agent or a soothing agent in a liquid medicine. And other additives such as preservatives, antioxidants, coloring agents and sweeting agents can be used as occassion arises. As an excipient vehicle, milk sugar, white sugar, D-mannitol, starch, crystal cellulose, more volatile silicic acid anhydride and so on are preferably exemplified. As a lubricant, magnesium stearate, calcium stearate, talc, colloidal silica and so on are preferably exemplified. As a bonding agent, crystal cellulose, white sugar, D-mannitol, dextrin, hydroxypropyl cellulose, hydroxypropylmethyl celluloce, polyvinyl pyrrolidone and so on are preferably exemplified. As a disintegrator, starch, carboxymethylcellulose, carboxymethylcellulose, calcium, croscarmellose sodium carboxymethyl starch sodium and so on are preferably exemplified. As a solvent, an injection solution, alcohol, propylene glycol, macrogol, sesame oil, corn oil and so on are preferably exemplifid. As a solubilizer, polyethylene glycol, propylene glycol, D-mannitol, benzyl benzoate, ethanol, trisaminomethane, cholesterol, triethanolamine, sodium carbonate, sodium citrate and so on are preferably exemplified. As a suspending agent, surfactants such as stearyltriethanolamine, sodium lauryl sulfate, laurylaminopropionic acid, lecithin, benzalkonium chloride, benzethonium chloride and monostearic acid glycerol, and hydrophilic high polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose, are preferably exemplified. As an isotonizing agent, sodium chloride, glycerol, D-mannitol and so on are preferably exemplified. As a buffer agent, buffer solutions of such as phosphate, acetate, carbonate and citric acid salt are preferably exemplified. As a soothing agent, benzyl alcohol is preferably exemplified. As a preservative, para-hydroxybenzoic esters, chlorobutanol, benzyl alcohol, phenethyl alcohol, dehydroacetic acid and sorbic acid are preferably exemplified. As an antioxidant, sulfite, ascorbic acid and so on are preferably exemplified.

The medicament comprising the compound (I) or a salt thereof has low toxicity and selectively and excellently inhibits a vascular permeability enhancer, which can be safely used to mammals (e.g. human, mouse, rat and rabbit), so that it is useful for preventing or treating a brain edema, an intracranial hemorrhage (especially its relapse) and a cerebral infarction caused by a cerebrovascular disease.

Furthermore, these medicaments can be used for treating or inhibiting the accompanying conditions, such as a emotional instability (e.g. depression, anxiety, insomnia and so on), a memory impairment (e.g. forgetfulness, dementia, and so on), or a mental disability (e.g. epilepsy, shizophrenia, and so on).

The medicament according to this invention can be safely administered orally or non-orally (such as administering to the affected part, the rectum and a vein), and the dosage depends on an administered subject, an administering route, the subject's symptoms and so on. In the case that it is orally administered to an adult brain edema patient, for example, it is desired to administer about 0.1 to 20 mg/kg, preferably about 0.5 to 10 mg/kg, calculated in terms of a compound (I) or a salt thereof, in one to several parts a day.

According to the present invention, it is possible to provide a safe medicament for inhibiting a vascular permeability enhancer comprising a compound (I) or a salt thereof, which can be used for preventing or treating a brain edema, an intracranial hemorrhage (especially its recurrence), a cerebral infarction and so on caused by a cerebrovascular disease.

DESCRIPTION OF PREFERRED EMBODIMENTS

The present invention is further described below with examples and experimental examples, but these are just concrete examples and do not limit the present invention, which may be changed within the limits of the present invention.

EXAMPLE 1

| | |
|---|---|
| (1) 6-[2-(9H-purin-6-yl)hydrazino]nebularine | 10.0 mg |
| (2) lactose | 60.0 mg |
| (3) corn starch | 35.0 mg |
| (4) gelatin | 3.0 mg |
| (5) magnesium stearate | 2.0 mg |
| | 110.0 mg/tablet |

A mixture of 10.0 mg of 6-[2-(9H-purin-6-yl)hydrazino] nebularine, 60.0 mg of milk sugar and 35.0 mg of corn starch was granulated through a 1 mm-mesh sieve using 0.03 ml of a 10 wt % gelatin solution (3.0 mg of gelatin), then dried at 40° C., and allowed to pass through the mesh again. The obtained granule was mixed with 2.0 mg of magnesium stearate and compressed. The obtained central tablet was sugar-coated with a suspension of cane sugar, titanium dioxide, talc and a gum arabic solution. The coated tablet was made glossy with beewax, completing producing a coating tablet.

EXAMPLE 2

| | |
|---|---|
| (1) 6-[2-(9H-purin-6-yl)hydrazino]nebularine | 10.0 mg |
| (2) lactose | 70.0 mg |
| (3) corn starch | 50.0 mg |
| (4) soluble starch | 7.0 mg |
| (5) magnesium stearate | 3.0 mg |
| | 140.0 mg/tablet |

10.0 mg of 6-[2-(9H-purin-6-yl )hydrazino]nebularine and 3.0 mg of magnesium stearate were granulated using 0.07 ml of a soluble starch aqueous solution (7.0 mg of soluble starch), then dried, and mixed with 70.0 mg of lactose and 50.0 mg of corn starch. The mixture was compressed so as to obtain a tablet.

EXAMPLE 3

| | |
|---|---|
| (1) 6-[2-(9H-purin-6-yl)hydrazino]nebularine | 5.0 mg |
| (2) salt | 20.0 mg |
| (3) distilled water | the whole quantity of 2 ml |

5.0 mg of 6-[2-(9H-purin-6-yl)hydrazino]nebularine and 20.0 mg of salt were dissolved in distilled water, to which distilled water was added so as to be totally 2.0 ml. The solution was filtrated and filled in a 2 ml ampul under an aseptic condition. The ampul was sterilized and sealed up, completing producing an injection solution.

EXPERIMENTAL EXAMPLE 1

Inhibitory Action to a Vascular Permeability Enhancer

To male Wistar rats (10–11 weeks old), pentobarbital anesthesia was given and then the compounds shown in Tables 1 and 2 were administered into their abdominal cavity (ip). 30 minutes later, 0.2 ml of 1% Evans Blue to 100 mg of weight was administered into the left femoral vein. 5 minutes later, 3 μg of 5'-deoxy-5'-methylthioadenosine (MTA), a factor of vascular permeability enhancement, was intradermally injected in the abdominal region, and then 8 minutes later, the extent of a extravasation of Evans Blue was measured, the inhibitory action to a vascular permeability enhancer was obtained by the following formula, and the results were shown in Tables 1 and 2. As a control, to the same kind of rat, only MTA was administered.

Inhibitory action to a vascular permeability enhancer (%) =

$$\frac{\text{extravasation area of the coloring matter after administering the present compound}}{\text{extravasation area of the coloring matter in the control}} \times 100$$

TABLE 1

| Compound No. | Compound name | Inhibitory effect to a vascular permeability enhancer (5 mg/kg, ip) |
|---|---|---|
| 1 | $N^6$-[1-(1-naphthyl)ethyl]adenosine | + |
| 2 | 6-[2-(1-naphthyl)hydrazino]nebularine | ++++ |
| 3 | $N^6$-[2-(4-1H-imidazolyl)ethyl]adenosine | ++++ |
| 4 | $N^6$[(4-amino-2-methyl-pyrimidin-5-yl)methyl]adenosine | ++++ |
| 5 | 6-[2-(2-naphthyl)hydrazino]nebularine | ++++ |
| 6 | 6-[2-(9H-purin-6-yl)hydrazino]nebularine | ++++ |
| 7 | 6-(2-benzoylhydrazino)nebularine | ++ |
| 8 | 6-[2-(4-amino-s-triazin-2-yl)hydrazino]nebularine | ++++ |
| 9 | 6-(2-benzylidenehydrazino)nebularine | ++++ |
| 10 | 6-[2-(2-phenylpyrimidin-4-yl)hydrazino]nebularine | ++++ |
| 11 | $N^6$-(2,5-dimethylpyrrol-1-yl)adenosine | ++++ |
| 12 | 2-(2-methoxyethoxy)adenosine | +++ |
| 13 | 2-anilinoadenosine | ++ |
| 14 | 6-mercaptonebularine | + |
| 15 | 2-(p-ethylanilino)adenosine | ++++ |
| 16 | 2-(m-methylanilino)adenosine | ++++ |
| 17 | 2-(p-carbamoylanilino)adenosine | + |
| 18 | 2-(3-chloro-4-methoxyanilino)adenosine | ++ |
| 19 | 2-(p-acetylanilino)adenosine | +++ |
| 20 | 2-anilino-$N^6$-(N,N-dimethylaminomethyl-idene)adenosine | + |

TABLE 2

| Compound No. | Compound name | Inhibitory effect to a vascular permeability enhancer (5 mg/kg, ip) |
|---|---|---|
| 21 | 2-(m-aminoanilino)adenosine | ++++ |
| 22 | 2-(p-ethylcarbamoylanilino)adenosine | ++ |
| 23 | 2-[p-(morpholinocarbonyl)anilino]adenosine | ++++ |
| 24 | 2-(3-pyridylamino)adenosine | + |
| 25 | 2-(2-quinolylamino)adenosine | +++ |
| 26 | 2-(m-propionylanilino)adenosine | +++ |
| 27 | 2-[(5-methylpyridin-2-yl)amino]adenosine | +++ |
| 28 | 2-[(2-methoxypyridin-5-yl)amino]adenosine | + |
| 29 | 2',3'-O-(1-ethoxyethylidene)adenosine-5'-(N-ethylcarboxamide | ++++ |
| 30 | 2-[(2-anilinopyridin-5-yl)amino]adenosine | +++ |
| 31 | 2-(p-n-propylanilino)adenosine | ++ |
| 32 | 2-(p-n-butylanilino)adenosine | ++++ |
| 33 | 2-anilino-2',3'-O-(1-methoxyethylidene)adenosine | ++++ |
| 34 | 2-(p-ethylanilino)-2',3'-ethoxyethylideneadenosine | + |
| 35 | 2-(4-acetyl-3-methoxyanilino)adenosine | ++ |
| 36 | 2-(4-acetyl-3-chloroanilino)adenosine | ++ |
| 37 | 2-(p-ethylanilino)-2',3'-O-(1-ethoxyethylidene)adenosine | ++++ |
| 38 | 2-[p-(1-methylpropyl)anilino]adenosine | ++ |
| 39 | $N^6$-[2-(2,5-dioxo-3,4,6-trimethyl-2H,5H-phenyl)ethyl]adenosine | +++ |
| 40 | 5'-deoxy-5'-methylsulfinyladenosine | ++++ |
| 41 | 2'-O-acetyladenosine-3',5'-monophosphate | +++ |
| 42 | 8-bromoadenosine | +++ |

++++, +++, ++ and + represent inhibition of 100%, 80–100%, 60–80% and 50–60%, respectively.

Tables 1 and 2 make it clear that a compound (I) or a salt thereof excellently inhibits a vascular permeability enhancer.

EXPERIMENTAL EXAMPLE 2

Stroke Preventive Effect

To male SHRSPs, which were 8 weeks old, the administration of the compound 2'3'-O-(1-ethoxyethylidene)-adenosine-5'-(N-ethylcarboxamide) (Compound No. 29) equivalent to 0.3 or 1.0 mg/kg/day mixed with a 3% salt-containing sample was started in the form of a feed. Through 60 days of the administration, their arterial blood pressure, body weight and feed intake were measured and their neurological symptoms were observed.

As a result, when the two groups to which the compound was administered did not show a decrease in blood pressure at the end of the administration. The period of the attack of stroke and the incidence of stroke in each group are shown in Table 3.

TABLE 3

| Experimental group | Number of days before attack of stroke (day) | Incidence in attack of stroke at the end of the experiment (%) |
|---|---|---|
| Control | 46.0 ± 2.3 | 100 |
| Feed mixed with the compound No. 29 of 0.3 mg/kg/day | 58.8 ± 2.2*** | 35 |
| Feed mixed with the compound No. 29 of 1.0 mg/kg/day | 58.4 ± 3.0** | 12* |

*p < 0.05,
**P < 0.01 and
***P < 0.001

The compound delayed the period of the attack of stroke and decreased the incidence of stroke in a dose-dependent manner.

As obvious from these results, the compound (No. 29) has the efficacy of preventing a stroke.

What is claimed is:

1. A method for treating or preventing cerebrovascular disease by inhibiting a vascular permeability enhancer, which comprises administering a pharmaceutically effective amount of a compound of the formula:

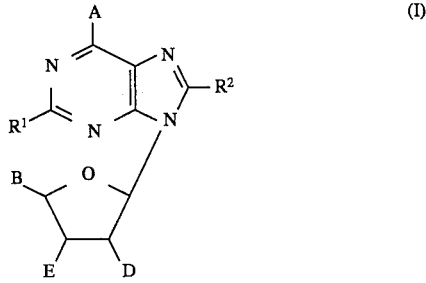

(I)

wherein

A is (i) a halogen atom, (ii) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group, or (iii) —Y=$R^4$ in which —Y= is —N= or —NHN= and $R^4$ is an optionally substituted divalent hydrocarbon group;

$R^1$ is (i) a hydrogen atom, (ii) a halogen atom, (iii) an optionally substituted hydrocarbon group, (iv) an optionally substituted heterocyclic group or (v) —Z—$R^5$ in which —Z— is —O—, —S— or —NH— and $R^5$ is a hydrogen atom, an optionally substituted hydrocarbon group or an optionally substituted aromatic heterocyclic group;

$R^2$ is a hydrogen atom, a halogen atom, or an optionally substituted heterocyclic group;

B is —W—$R^6$ in which —W— is —$CH_2$—, >C=O or >C=S and $R^6$ is hydroxyl, or an optionally substituted alkoxy, acyloxy, alkylsulfinyl, alkylsulfonyl, O-phosphono or amino group, or B together with E may optionally form a cyclic phosphoric ester; and D and E are independently a hydrogen atom, an optionally substituted amino group, an azido group, a halogen atom or an optionally protected hydroxyl group, or a pharmaceutically acceptable salt thereof.

2. A method of claim 1, wherein the disease is a brain edema, an intracranial hemorrhage or a cerebral infarction.

3. A method of claim 1, wherein the disease is a traumatic brain edema or a traumatic intracranial hemorrhage.

4. A method of claim 1, wherein

A is (i) —X—$R^3$ in which —X— is —O—, —S—, —NH— or —NHNH— and $R^3$ is a hydrogen atom, an acyl group, an optionally substituted hydrocarbon group or an optionally substituted aromatic heterocyclic group or (ii) —Y=$R^4$ in which —Y= is —N= or —NHN= and $R^4$ is an optionally substituted divalent hydrocarbon group;

$R^1$ is (i) a hydrogen atom, or (ii) —Z—$R^5$ in which —Z— is —O—, —S— or —NH—, and $R^5$ is a hydrogen atom, an optionally substituted hydrocarbon group or an optionally substituted aromatic heterocyclic group;

$R^2$ is a hydrogen atom, a halogen atom or an optionally substituted hydrocarbon group; and D and E are independently a hydrogen atom, an amino group, an azido group, a halogen atom or an optionally protected hydroxyl group.

5. A method of claims 1 or 4, wherein the substituent which the divalent hydrocarbon group may optionally have is a substituted amino group, an optionally substituted aryl group or an optionally substituted aromatic heterocyclic group.

6. A method of claims 1 or 4, wherein —X— is —NH— or —NHNH—, and $R^3$ is (i) a hydrogen atom, (ii) an acyl group, (iii) an optionally substituted $C_{1-6}$alkyl group, (iv) an optionally substituted $C_{6-14}$aryl group or (v) an optionally substituted 5- to 14-membered monocyclic or condensed polycyclic aromatic heterocyclic group.

7. A method of claims 1 or 4, wherein $R^4$ is a divalent lower aliphatic hydrocarbon group optionally having one substituent selected from the group consisting of (i) a mono- or di-$C_{1-6}$alkylamino group, (ii) an optionally substituted $C_{6-14}$aryl group and (iii) an optionally substituted 5- to 14-membered monocyclic or condensed polycyclic aromatic heterocyclic group.

8. A method of claims 1 or 4, wherein A is —NHNH—$R^3{}_a$ in which $R^3{}_a$ is a 5- to 14-membered monocyclic or condensed polycyclic aromatic heterocyclic group optionally having one to three substituents selected from the group consisting of amino, mono-$C_{1-6}$alkylamino, di-$C_{1-6}$alkylamino, anilino, halogen, cyano, hydroxyl, $C_{1-6}$alkyl, $C_{1-6}$alkoxy, $C_{1-6}$alkyl-carbonyl, carbamoyl, mono-$C_{1-6}$alkylcarbamoyl, di-$C_{1-6}$alkylcarbamoyl, mono- or di-$C_{6-14}$arylcarbamoyl and phenyl.

9. A method of claims 1 or 4, wherein A is —$NH_2$.

10. A method of claims 1 or 4, wherein —Z— is —O— or —NH—, and $R^5$ is (i) an optionally substituted $C_{1-6}$alkyl group, (ii) an optionally substituted $C_{6-14}$aryl group or (iii) an optionally substituted 5- to 14-membered monocyclic or condensed polycyclic aromatic heterocyclic group.

11. A method of claims 1 or 4, wherein $R^1$ is a hydrogen atom.

12. A method of claims 1 or 4, wherein $R^1$ is —NH—$R^{5\,a}$ in which $R^{5\,a}$ is a $C_{6-14}$aryl group optionally having one to three substituents selected from the group consisting of amino, mono-$C_{1-6}$alkylamino, di-$C_{1-6}$alkylamino, anilino, halogen, cyano, hydroxyl, $C_{1-6}$alkyl, $C_{1-6}$alkoxy, $C_{1-6}$alkylcarbonyl, 5- or 6-membered heterocycle-carbonyl, carbamoyl, mono-$C_{1-6}$alkylcarbamoyl, di-$C_{1-6}$alkylcarbamoyl and mono- or di-$C_{6-14}$arylcarbamoyl.

13. A method of claims 1 or 4, wherein $R^2$ is a hydrogen atom.

14. A method of claims 1 or 4, wherein $R^6$ is a hydroxyl group, a $C_{6-14}$aryl-carbonyloxy group, a $C_{1-6}$alkylsulfinyl group, an amino group, a mono-$C_{1-6}$alkylamino group, a di-$C_{1-6}$alkylamino group or an anilino group.

15. A method of claims 1 or 4, wherein W is >C=O, and $R^6$ is a mono- or di-$C_{1-6}$ alkylamino group.

16. A method of claims 1 or 4, wherein B is —CH$_2$OH.

17. A method of claims 1 or 4, wherein D and E are independently an optionally protected hydroxyl group.

18. A method of claim 17, wherein the protective group of an optionally protected hydroxyl group is formyl, $C_{1-6}$alkylcarbonyl, benzoyl, nicotinoyl, $C_{1-6}$alkyl, benzyl, $C_{3-6}$cycloalkyl-carbonyl, 2',3'-O-($C_{1-6}$alkylidene), 2',3'-O-($C_{1-6}$alkoxy-$C_{1-6}$alkylidene) or 2',3'-O-($C_{4-7}$cyclo alkylidene).

19. A method of claim 17, wherein the protective group of an optionally protected hydroxyl group is 2',3'-O-($C_{1-6}$alkoxy-$C_{1-6}$alkylidene).

20. A method of claims 1 or 4, wherein D and E are hydroxyl groups.

21. A method of claim 1, wherein

A is —NHNH—$R^{3\,b}$ in which $R^{3\,b}$ is a 5- to 14-membered monocyclic or condensed polycyclic aromatic heterocyclic group optionally having one to three substituents selected from the group consisting of a $C_{1-6}$alkyl group, an amino group and a phenyl group;

$R^1$ and $R^2$ are hydrogen atoms;

B is —CH$_2$OH; and

D and E are independently an optionally protected hydroxyl group.

22. A method of claim 1, wherein

A is —NH$_2$;

$R^1$ and $R^2$ are hydrogen atoms;

B is of the formula:

(II)

in which $R^{7\,a}$ and $R^{8\,a}$ are independently (i) a hydrogen atom, (ii) a $C_{1-6}$alkyl group, (iii) a formyl group, (iv) a $C_{1-6}$alkyl-carbonyl group, (v) a $C_{7-16}$aralkyl-carbonyl group or (vi) a nicotinoyl group, or $R^{7\,a}$ and $R^{8\,a}$ taken together with the adjacent nitrogen atom form a 5- or 6-membered nitrogen-containing heterocyclic group; and D and E are independently an optionally protected hydroxyl group.

23. A method of claims 21 or 22, wherein D and E are hydroxyl groups.

24. A method of claim 1, wherein the compound (I) is one of the formula:

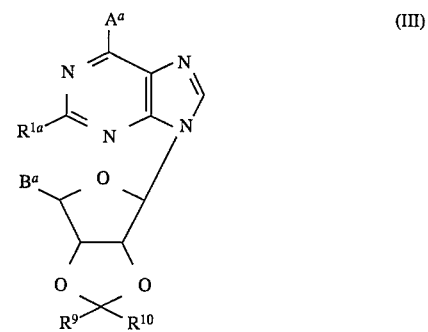

(III)

wherein $A^a$ is (i) —NH$_2$ or (ii) —NHNH—$R^{3\,b}$ in which $R^{3\,b}$ is a 5- to 14-membered monocyclic or condensed polycyclic aromatic heterocyclic group optionally having one to three substituents selected from the group consisting of a $C_{1-6}$alkyl group, an amino group and a phenyl group;

$R^{1\,a}$ is (i) a hydrogen atom or (ii) —NH—$R^{5\,a}$ in which $R^{5\,a}$ is a $C_{6-14}$aryl group optionally having one to three substituents selected from the group consisting of amino, mono-$C_{1-6}$ alkylamino, di-$C_{1-6}$alkylamino, anilino, halogen, cyano, hydroxyl, $C_{1-6}$alkyl, $C_{1-6}$alkoxy, $C_{1-6}$alkyl-carbonyl, 5- or 6-membered heterocycle-carbonyl, carbamoyl, mono-$C_{1-6}$alkylcarbamoyl, di-$C_{1-6}$alkylcarbamoyl and mono- or di-$C_{6-14}$arylcarbamoyl;

$B^a$ is —CO—$R^{6\,a}$ in which $R^{6\,a}$ is a mono- or di-$C_{1-6}$alkylamino group; and $R^9$ and $R^{10}$ are independently a hydrogen atom, a $C_{1-6}$alkyl group or a $C_{1-6}$alkoxy group.

25. A method of claim 1, wherein the compound (I) is 6-[2-(9H-purin-6-yl)hydrazino]nebularine.

26. A method of claim 1, wherein the compound (I) is 6-[2-(4-amino-s-triazin-2-yl)hydrazino]nebularine.

27. A method of claim 1, wherein the compound (I) is 2-[p-(morpholinocarbonyl)anilino]adenosine.

28. A method of claim 1, wherein the comound (I) is 2'-3'-O-(1-ethoxyethylidene)adenosine-5'-(N-ethylcarboxamide).

* * * * *

UNITED STATES PATENT AND TRADEMARK OFFICE
CERTIFICATE OF CORRECTION

PATENT NO. : 5,604,210

DATED : February 18, 1997

INVENTOR(S): AKINOBU NAGAOKA, ET AL.     Page 1 of 3

It is certified that error appears in the above-identified patent and that said Letters Patent is hereby corrected as shown below:

Title page, item

[56] ABSTRACT

Line 1, "treatment" should read --treatment of--.

COLUMN 1

Line 23, "disorder" should be deleted.
Line 43, "EP-0526866-All" should read --EP-0526866-Al--.

COLUMN 3

Line 31, "$C_{64}$aryl" should read --$C_{6-14}$aryl--.

COLUMN 5

Line 22, "(9H-purine-" should read --(9H-purin---.

COLUMN 7

Line 57, "4-morphorinocarbonyl," should read
   --4-morpholinocarbonyl,--.
Line 59, "4-morphorinocarbonyl)" should read
   --4-morpholinocarbonyl)--.

COLUMN 9

Line 50, "group" should read --groups--.

UNITED STATES PATENT AND TRADEMARK OFFICE
CERTIFICATE OF CORRECTION

PATENT NO. : 5,604,210

DATED : February 18, 1997

INVENTOR(S): AKINOBU NAGAOKA, ET AL.

It is certified that error appears in the above-identified patent and that said Letters Patent is hereby corrected as shown below:

COLUMN 10

Line 54, "(ill)" should read --(iii)--.

COLUMN 12

Line 59, "is" should read --are--.

COLUMN 13

Line 39, "sweeting" should read --sweetening--.
   Line 53, "exemplifid." should read --exemplified.--.

COLUMN 14

Line 10, "to" should read --in--.

COLUMN 16

Table 2, "(N-ethylcarboxamide" should read
     --(N-ethylcarboxamide)--.

COLUMN 17

Line 12, "when" should be deleted.

UNITED STATES PATENT AND TRADEMARK OFFICE
CERTIFICATE OF CORRECTION

PATENT NO. : 5,604,210

DATED : February 18, 1997

INVENTOR(S): AKINOBU NAGAOKA, ET AL.

It is certified that error appears in the above-identified patent and that said Letters Patent is hereby corrected as shown below:

COLUMN 18

Line 56, "–$R^3$" should read -- –$R^{3a}$ --.
Line 57, "$\underline{a}$" should be deleted.

COLUMN 19

Line 5, "–$R^5$" should read -- –$R^{5a}$ --.
Line 6, "$\underline{a}$" should be deleted.

COLUMN 20

Line 53, "comound" should read --compound--.

Signed and Sealed this

Twenty-first Day of October 1997

Attest:

BRUCE LEHMAN

Attesting Officer

Commissioner of Patents and Trademarks